United States Patent
Liu et al.

(10) Patent No.: US 11,866,790 B2
(45) Date of Patent: Jan. 9, 2024

(54) COMBINATION OF DNA METHYLATION MARKERS AND USE THEREOF, PRIMERS, PROBES AND KIT FOR EARLY DETECTION OF OVARIAN CANCER

(71) Applicant: BEIJING ORIGINPOLY BIO-TEC CO., LTD., Beijing (CN)

(72) Inventors: Pei Liu, Beijing (CN); Linhai Wang, Beijing (CN)

(73) Assignee: BEIJING ORIGINPOLY BIO-TEC CO., LTD, Beijing (CN)

( * ) Notice: Subject to any disclaimer, the term of this patent is extended or adjusted under 35 U.S.C. 154(b) by 0 days.

(21) Appl. No.: 17/871,119

(22) Filed: Jul. 22, 2022

(65) Prior Publication Data
US 2023/0279497 A1 Sep. 7, 2023

Related U.S. Application Data

(63) Continuation of application No. PCT/CN2022/095437, filed on Jun. 9, 2022.

(30) Foreign Application Priority Data

Mar. 3, 2022 (CN) .......................... 202210208334.2

(51) Int. Cl.
*C12Q 1/6886* (2018.01)
(52) U.S. Cl.
CPC ..... *C12Q 1/6886* (2013.01); *C12Q 2600/154* (2013.01)
(58) Field of Classification Search
None
See application file for complete search history.

(56) References Cited

U.S. PATENT DOCUMENTS

2022/0076779 A1* 3/2022 Feinberg ................ G16B 20/20

FOREIGN PATENT DOCUMENTS

| CN | 109069670 A | 12/2018 | |
|---|---|---|---|
| CN | 113755603 A | 12/2021 | |
| TW | 201632629 A | 9/2016 | |
| WO | WO-2012031008 A2 * | 3/2012 | ........... C12Q 1/6806 |

\* cited by examiner

*Primary Examiner* — Katherine D Salmon
(74) *Attorney, Agent, or Firm* — Nixon Peabody LLP; Mark J. FitzGerald (57) ABSTRACT

The present invention discloses a combination of DNA methylation markers and the use thereof, primers, probes and a kit for early detection of ovarian cancer, wherein the combination of DNA methylation markers comprises at least one methylated fragment of each of four genes, including PCDHB18P, CDO1, HOXA9 and LYPD5. The detection primers and kit obtained for the methylated regions of the target genes can significantly improve the sensitivity of ovarian cancer detection, and meanwhile maintain a high specificity for normal ovarian cells and benign ovarian tumors. The detection primers and probes detect patients with possible gynecological malignant tumors early through molecular epigenetic methods using methylation detection technology, and the result is very accurate, and can provide clinicians with auxiliary diagnostic reference for early prophylactic treatment.

8 Claims, 2 Drawing Sheets

Specification includes a Sequence Listing.

```
                            SEQUENCE LISTING

Sequence total quantity: 51
SEQ ID NO: 1           moltype = DNA   length = 102
FEATURE                Location/Qualifiers
source                 1..102
                       mol_type = other DNA
                       organism = synthetic construct
SEQUENCE: 1
actggaccaa tccctggatc gagaaaaggt gtctgagttt agtttaacgc taacagccgt   60
ggatggcggg tctccgccca ggtctgggac tacactgatt aa                     102

SEQ ID NO: 2           moltype = DNA   length = 123
FEATURE                Location/Qualifiers
source                 1..123
                       mol_type = other DNA
                       organism = synthetic construct
SEQUENCE: 2
aaatgaatat aacatcacca tcaccgtgac cgacttgggg acacccaggc tgaaaaccga   60
gcacaacata accgtgctgg tctccgacgt caatgacaac gcccccatct tcacccaaac   120
ctc                                                                123

SEQ ID NO: 3           moltype = DNA   length = 83
FEATURE                Location/Qualifiers
source                 1..83
                       mol_type = other DNA
                       organism = synthetic construct
SEQUENCE: 3
agacagagac tcaggcacca acgcccaggt cacctactcg ctgctgccgc cccaggaccc   60
gcacctgccc ctcacctccc tgg                                          83

SEQ ID NO: 4           moltype = DNA   length = 100
FEATURE                Location/Qualifiers
source                 1..100
                       mol_type = other DNA
                       organism = synthetic construct
SEQUENCE: 4
tcttgggtgg ctctccgcct cgtcctccct ccgagggccg ttggtacatt cctagtgact   60
ccaagcgctt aaaaggggcc cgggaggatg aaccccacag                        100

SEQ ID NO: 5           moltype = DNA   length = 78
FEATURE                Location/Qualifiers
source                 1..78
                       mol_type = other DNA
                       organism = synthetic construct
SEQUENCE: 5
gtctcttgct gtctctgcga cgacatcctt acgtttcggc actctaatgc tgggtttgtg   60
cgtgtgtgtc tgcttagc                                                78

SEQ ID NO: 6           moltype = DNA   length = 79
FEATURE                Location/Qualifiers
source                 1..79
                       mol_type = other DNA
                       organism = synthetic construct
SEQUENCE: 6
gctcgctcag ctcctccacc gcagcccagc agtgagacgc gcgcgcagcc agctccccac   60
gagatggaac agaccgaag                                               79

SEQ ID NO: 7           moltype = DNA   length = 93
FEATURE                Location/Qualifiers
source                 1..93
                       mol_type = other DNA
                       organism = synthetic construct
SEQUENCE: 7
gccagctgat gagaaaggcg ggctgggcgc gcgtgtgcgt ggggtcgagg gccggggacc   60
gagcgcgccg cacaaccaac caggccctca aaa                               93

SEQ ID NO: 8           moltype = DNA   length = 107
FEATURE                Location/Qualifiers
source                 1..107
                       mol_type = other DNA
                       organism = synthetic construct
SEQUENCE: 8
```

```
cagtctaacc tttccaagtc ctcgtaaatt tttacagctg ggagccacgg cgaggcaaac    60
gaatctgttg gtcgtttccg acttcccgcc agcctgtgtg gcttctg                107

SEQ ID NO: 9              moltype = DNA   length = 85
FEATURE                   Location/Qualifiers
source                    1..85
                          mol_type = other DNA
                          organism = synthetic construct
SEQUENCE: 9
tttatgtgag gggctccgct ggccgcactc gcacgcggga cccgcgcctt cttgatggcg    60
tgattaattg tgatataaaa tagtc                                         85

SEQ ID NO: 10             moltype = DNA   length = 107
FEATURE                   Location/Qualifiers
source                    1..107
                          mol_type = other DNA
                          organism = synthetic construct
SEQUENCE: 10
tgaaatttga taactgaaaa cgaagtatgc catctgtttc cgttatcagt ttattgctct    60
cacctccgca cgcactcttc aatatacgct ccctgctaaa gggattc                 107

SEQ ID NO: 11             moltype = DNA   length = 70
FEATURE                   Location/Qualifiers
source                    1..70
                          mol_type = other DNA
                          organism = synthetic construct
SEQUENCE: 11
ttcccacagg tcactgggcc gaatgagcgt gcgctcctga tccgctttgc gcatcccagt    60
gattcttggg                                                         70

SEQ ID NO: 12             moltype = DNA   length = 107
FEATURE                   Location/Qualifiers
source                    1..107
                          mol_type = other DNA
                          organism = synthetic construct
SEQUENCE: 12
ggtgtgtgca atattatgtg cgtgatagag ccaaggatgt gccctaccgt gcgaatggtg    60
acgttgcgtc tgtatgagag tgcacgtgcc acggctggga tgtcttg                107

SEQ ID NO: 13             moltype = DNA   length = 28
FEATURE                   Location/Qualifiers
source                    1..28
                          mol_type = other DNA
                          organism = synthetic construct
SEQUENCE: 13
atccaaaatt ggattaattt ttggatcg                                      28

SEQ ID NO: 14             moltype = DNA   length = 31
FEATURE                   Location/Qualifiers
source                    1..31
                          mol_type = other DNA
                          organism = synthetic construct
SEQUENCE: 14
tttaggttca atataatccc aaacctaaac g                                  31

SEQ ID NO: 15             moltype = DNA   length = 31
FEATURE                   Location/Qualifiers
source                    1..31
                          mol_type = other DNA
                          organism = synthetic construct
SEQUENCE: 15
ccgccataac gttaatagtc gtggatggcg g                                  31

SEQ ID NO: 16             moltype = DNA   length = 36
FEATURE                   Location/Qualifiers
source                    1..36
                          mol_type = other DNA
                          organism = synthetic construct
SEQUENCE: 16
ataataataa aaatgaatat aatattatta ttatcg                             36

SEQ ID NO: 17             moltype = DNA   length = 34
FEATURE                   Location/Qualifiers
source                    1..34
                          mol_type = other DNA
                          organism = synthetic construct
SEQUENCE: 17
tttttatttt aaaatttaaa taaaaataaa aacg                               34
```

-continued

```
SEQ ID NO: 18           moltype = DNA    length = 30
FEATURE                 Location/Qualifiers
source                  1..30
                        mol_type = other DNA
                        organism = synthetic construct
SEQUENCE: 18
ttaacgaatc gtgttggttt tcgacgttaa                                          30

SEQ ID NO: 19           moltype = DNA    length = 31
FEATURE                 Location/Qualifiers
source                  1..31
                        mol_type = other DNA
                        organism = synthetic construct
SEQUENCE: 19
ttaataccag atagagattt aggtattaac g                                        31

SEQ ID NO: 20           moltype = DNA    length = 32
FEATURE                 Location/Qualifiers
source                  1..32
                        mol_type = other DNA
                        organism = synthetic construct
SEQUENCE: 20
tatttgttcc aaaaaaataa aaacaaata cg                                        32

SEQ ID NO: 21           moltype = DNA    length = 28
FEATURE                 Location/Qualifiers
source                  1..28
                        mol_type = other DNA
                        organism = synthetic construct
SEQUENCE: 21
taaaacgtta ttcgttgttg tcgtttta                                            28

SEQ ID NO: 22           moltype = DNA    length = 24
FEATURE                 Location/Qualifiers
source                  1..24
                        mol_type = other DNA
                        organism = synthetic construct
SEQUENCE: 22
aaaaaccttt tgggtggttt ttcg                                                24

SEQ ID NO: 23           moltype = DNA    length = 28
FEATURE                 Location/Qualifiers
source                  1..28
                        mol_type = other DNA
                        organism = synthetic construct
SEQUENCE: 23
ggaggatgct ataaaattca tcctcccg                                            28

SEQ ID NO: 24           moltype = DNA    length = 30
FEATURE                 Location/Qualifiers
source                  1..30
                        mol_type = other DNA
                        organism = synthetic construct
SEQUENCE: 24
aacgacctcg ttttttttc gagggtcgtt                                           30

SEQ ID NO: 25           moltype = DNA    length = 26
FEATURE                 Location/Qualifiers
source                  1..26
                        mol_type = other DNA
                        organism = synthetic construct
SEQUENCE: 25
caaaaacgtt ttttgttgtt tttgcg                                              26

SEQ ID NO: 26           moltype = DNA    length = 25
FEATURE                 Location/Qualifiers
source                  1..25
                        mol_type = other DNA
                        organism = synthetic construct
SEQUENCE: 26
tgtgtgtgct aaacaaacac acacg                                               25

SEQ ID NO: 27           moltype = DNA    length = 27
FEATURE                 Location/Qualifiers
source                  1..27
                        mol_type = other DNA
                        organism = synthetic construct
SEQUENCE: 27
aaaatacttt ttacgtttcg gtatttt                                             27
```

```
SEQ ID NO: 28           moltype = DNA   length = 28
FEATURE                 Location/Qualifiers
source                  1..28
                        mol_type = other DNA
                        organism = synthetic construct
SEQUENCE: 28
ataaaaagtt cgtttagttt ttttatcg                                      28

SEQ ID NO: 29           moltype = DNA   length = 27
FEATURE                 Location/Qualifiers
source                  1..27
                        mol_type = other DNA
                        organism = synthetic construct
SEQUENCE: 29
agatggactt cgatctattc catctcg                                       27

SEQ ID NO: 30           moltype = DNA   length = 27
FEATURE                 Location/Qualifiers
source                  1..27
                        mol_type = other DNA
                        organism = synthetic construct
SEQUENCE: 30
taactacgtg agacgcgcgc gtagtta                                       27

SEQ ID NO: 31           moltype = DNA   length = 28
FEATURE                 Location/Qualifiers
source                  1..28
                        mol_type = other DNA
                        organism = synthetic construct
SEQUENCE: 31
cctttctcgt tagttgatga gaaaggcg                                      28

SEQ ID NO: 32           moltype = DNA   length = 33
FEATURE                 Location/Qualifiers
source                  1..33
                        mol_type = other DNA
                        organism = synthetic construct
SEQUENCE: 32
tataattatt ttaaaaacct aattaattat acg                                33

SEQ ID NO: 33           moltype = DNA   length = 26
FEATURE                 Location/Qualifiers
source                  1..26
                        mol_type = other DNA
                        organism = synthetic construct
SEQUENCE: 33
ccacgcatgg gcgcgcgtgt gcgtgg                                        26

SEQ ID NO: 34           moltype = DNA   length = 32
FEATURE                 Location/Qualifiers
source                  1..32
                        mol_type = other DNA
                        organism = synthetic construct
SEQUENCE: 34
aaaacttata gtttaatttt tttaagtttt cg                                 32

SEQ ID NO: 35           moltype = DNA   length = 29
FEATURE                 Location/Qualifiers
source                  1..29
                        mol_type = other DNA
                        organism = synthetic construct
SEQUENCE: 35
ttagtttgca aaaaccacac aaactaacg                                     29

SEQ ID NO: 36           moltype = DNA   length = 29
FEATURE                 Location/Qualifiers
source                  1..29
                        mol_type = other DNA
                        organism = synthetic construct
SEQUENCE: 36
attcgtttat tacggcgagg taaacgaat                                     29

SEQ ID NO: 37           moltype = DNA   length = 27
FEATURE                 Location/Qualifiers
source                  1..27
                        mol_type = other DNA
                        organism = synthetic construct
SEQUENCE: 37
```

```
aaaccccctct ttatgtgagg ggtttcg                                              27

SEQ ID NO: 38            moltype = DNA   length = 36
FEATURE                  Location/Qualifiers
source                   1..36
                         mol_type = other DNA
                         organism = synthetic construct
SEQUENCE: 38
tgattaatta actattttat atcacaatta atcacg                                     36

SEQ ID NO: 39            moltype = DNA   length = 35
FEATURE                  Location/Qualifiers
source                   1..35
                         mol_type = other DNA
                         organism = synthetic construct
SEQUENCE: 39
aacgcgaatt cgtattcgta cgcgggattc gcgtt                                      35

SEQ ID NO: 40            moltype = DNA   length = 30
FEATURE                  Location/Qualifiers
source                   1..30
                         mol_type = other DNA
                         organism = synthetic construct
SEQUENCE: 40
ttttcaattg aaatttgata attgaaaacg                                            30

SEQ ID NO: 41            moltype = DNA   length = 28
FEATURE                  Location/Qualifiers
source                   1..28
                         mol_type = other DNA
                         organism = synthetic construct
SEQUENCE: 41
tttttgaaa tccctttaac aaaaaacg                                               28

SEQ ID NO: 42            moltype = DNA   length = 36
FEATURE                  Location/Qualifiers
source                   1..36
                         mol_type = other DNA
                         organism = synthetic construct
SEQUENCE: 42
attaaaaagt ttttattttc gtacgtattt tttaat                                     36

SEQ ID NO: 43            moltype = DNA   length = 28
FEATURE                  Location/Qualifiers
source                   1..28
                         mol_type = other DNA
                         organism = synthetic construct
SEQUENCE: 43
acccaatttt ttataggtta ttgggtcg                                              28

SEQ ID NO: 44            moltype = DNA   length = 29
FEATURE                  Location/Qualifiers
source                   1..29
                         mol_type = other DNA
                         organism = synthetic construct
SEQUENCE: 44
tattttagcc caaaaatcac taaaatacg                                             29

SEQ ID NO: 45            moltype = DNA   length = 28
FEATURE                  Location/Qualifiers
source                   1..28
                         mol_type = other DNA
                         organism = synthetic construct
SEQUENCE: 45
aacgaatagc gtgcgttttt gattcgtt                                              28

SEQ ID NO: 46            moltype = DNA   length = 30
FEATURE                  Location/Qualifiers
source                   1..30
                         mol_type = other DNA
                         organism = synthetic construct
SEQUENCE: 46
cacataatgg tgtgtgtaat attatgtgcg                                            30

SEQ ID NO: 47            moltype = DNA   length = 23
FEATURE                  Location/Qualifiers
source                   1..23
                         mol_type = other DNA
                         organism = synthetic construct
```

```
SEQUENCE: 47
gttgggacaa aacatcccaa ccg                                              23

SEQ ID NO: 48         moltype = DNA  length = 31
FEATURE               Location/Qualifiers
source                1..31
                      mol_type = other DNA
                      organism = synthetic construct
SEQUENCE: 48
acgcaacgtc gtgcgaatgg tgacgttgcg t                                     31

SEQ ID NO: 49         moltype = DNA  length = 20
FEATURE               Location/Qualifiers
source                1..20
                      mol_type = other DNA
                      organism = synthetic construct
SEQUENCE: 49
aggttaaata tagttgttga                                                  20

SEQ ID NO: 50         moltype = DNA  length = 17
FEATURE               Location/Qualifiers
source                1..17
                      mol_type = other DNA
                      organism = synthetic construct
SEQUENCE: 50
caacccaaac ccccaac                                                     17

SEQ ID NO: 51         moltype = DNA  length = 18
FEATURE               Location/Qualifiers
source                1..18
                      mol_type = other DNA
                      organism = synthetic construct
SEQUENCE: 51
tagttggggg tttgggtt                                                    18
```

COMBINATION OF DNA METHYLATION MARKERS AND USE THEREOF, PRIMERS, PROBES AND KIT FOR EARLY DETECTION OF OVARIAN CANCER

CROSS-REFERENCE TO RELATED APPLICATIONS

This application claims benefit to International Patent Application No. PCT/CN2022/095437 filed on Jun. 9, 2022 which claims benefit under 35 U.S.C. § 119(b) of CN Application No. CN202210208334.2, filed on 3 Mar. 2022, the contents of each of which are incorporated herein by reference in their entireties.

SEQUENCE LISTING

The instant application contains a Sequence Listing which has been submitted electronically in XML format and is hereby incorporated by reference in its entirety. Said XML copy, created on Sep. 30, 2022, is named 070019-192390USC1_SL.xml and is 47,195 bytes in size.

TECHNICAL FIELD

The present invention relates to the field of genetic detection technology, in particular to a combination of DNA methylation markers and the use thereof, and primers, probes and a kit for early detection of ovarian cancer which are designed for the markers.

BACKGROUND ART

In China, the incidence of ovarian cancer ranks third in gynecological malignant tumors, accounting for about 23% of all female reproductive tract tumors, and shows an increasing trend year by year. About 25,000 women die from ovarian cancer every year in China, which ranks first in malignant tumors. Because the ovary is deep in the pelvic cavity, small in size, and lacks typical symptoms, ovarian cancer is difficult to detect early. 60%-70% patients are in the advanced stage as they are diagnosed, and the 5-year survival rate thereof is 20%-30%. During the surgery on the patients with ovarian cancer, less than 30% of the tumor was found to be confined to the ovary, and most of the tumors had spread to the pelvic and abdominal organs. The 5-year survival rate of patients with stage I ovarian cancer may be up to 90%, but early diagnosis thereof is very difficult.

At present, methods for monitoring the treatment and recurrence of ovarian cancer mainly include transvaginal ultrasound (TVUS), CA125 blood test, CT (scientific name: contrast-enhanced computed tomography), magnetic resonance imaging (MM), histopathological examination, etc. TVUS can help identify potential ovarian hyperplasia and determine whether they are solid proliferation or cysts (cysts are noncancerous, fluid-filled sacs) by using ultrasound echoes to transmit imaging images. If a solid mass is found, a doctor may request a biopsy to determine whether the mass is benign or malignant. B-ultrasound, which is fast, economical, non-invasive and repeatable, is the preferred examination method. However, the morphology, internal structure of small ovarian mass and its relationship with surrounding tissues are often unclear, and it is difficult to detect solid tumors with a diameter of <1 cm.

The CA125 blood test is used to measure the amount of CA125 protein in the blood. Many patients with ovarian cancer have an elevated level of CA125 in the blood. Not every patient with ovarian cancer has an elevated level of CA125 in the blood. According to the data from the Ovarian Cancer Research Fund Alliance (OCRFA), approximately 80% of patients with advanced ovarian cancer have a high level of CA125, and 50% of patients have a high level of CA125 in the early stages of the disease. Moreover, patients with other diseases such as pelvic inflammatory disease and endometriosis also have an elevated level of CA125 in the blood.

A CT scan is used to scan the abdomen with special X-rays. The results are processed by a computer, and cross-sectional images are generated so that doctors can see various parts of the abdominal cavity and pelvis. Through CT examination, pelvic tumors can be located and characterized, and it can be known whether there is metastasis in hepatic, pneumal and retroperitoneal lymph nodes. In addition, through pelvic lymphadenography, it can be determined whether ovarian tumors have lymphatic metastasis. However, there is no significant difference in CT between primary ovarian tumors and metastatic tumors. When diagnosing ovarian cancer, regardless of the presence or absence of primary foci, it should be differentiated from metastatic tumors, and a comprehensive and detailed investigation should be carried out.

MM has a high resolution for soft tissues, allows imaging in multiple planes, and is non-invasive. MRI has a large advantage in observing the depth of endometrial lesions invading the myometrium and the boundary between cervical tumors and bladder or rectum tumors, and plays an important role in the diagnosis and differential diagnosis of pelvic lesions caused by ovarian cancer. However, the cost of MRI is also higher than that of CT. For patients with intrauterine devices, MM can only be done after removal of the intrauterine devices.

Abdominal or posterior fornix puncture to take ascites for cytological examination is helpful for the diagnosis of ovarian malignancy. Biopsy results are an important factor in the final diagnosis of ovarian cancer. Although the final histopathology is the gold standard, most ovarian cancers by then are in the middle and late stages, which cannot achieve the purpose of early diagnosis.

Non-invasiveness and low cost are ideal features for early cancer screening. However, for ovarian cancer, there is currently no effective early screening method in clinical practice. DNA methylation is a modification mode of epigenetics. Research reports that DNA methylation can affect the gene expression and silence of normal mammalian cells; at the same time, it has been found in human tumor research that DNA methylation usually leads to changes of CpG island in the promoter region of a tumor suppressor gene. Hypermethylation or hypomethylation in the promoter region of a tumor suppressor gene may lead to cell transformation, making the DNA methylation status become a potential marker for tumor detection.

DNA methylation mainly occurs in the promoter region of a gene, and is usually closely related to the inactivation of the expression of a tumor suppressor gene. The main methods currently used in the detection for gene methylation include: Methylation-specific PCR (MSP), Bisulfite sequencing PCR (BSP) and High Resolution Melting (HRM), etc. Methylation-specific PCR mainly relies on the binding of primers with target templates for PCR amplification to detect methylated sites; the bisulfite sequencing PCR relies on sequencing primers for PCR amplification, and subsequent sequencing is performed on this basis to realize the detection of methylated sites; the high-resolution melting distinguishes between methylated and non-methylated status mainly through the change of the melting temperature caused by the change of the CG content in the sample. Each method has its own characteristics. The BSP has high accuracy and is easy for intuitive interpretation, but has low sensitivity, relatively more cumbersome operation, and high cost; the HRM method has relatively low sensitivity, and has slightly complicated analysis for the results; and the PCR has high detection sensitivity and relatively low requirements for samples, at the same time, has short detection time, has low cost, and has results easy to interpret.

With the deepening of tumor research, it is gradually found that the tissue biopsy technology has certain limitations in the process of cancer diagnosis and treatment. The major limitations are as follows: tumors are heterogeneous; it is very difficult to obtain tissues from some patients for various reasons; there is also a risk of accelerating tumor metastasis when undergoing a puncture biopsy; and the hysteresis of tissue biopsy is also detrimental to the treatment for patients. Therefore, the tissue biopsy technology has higher requirements for the diagnosis and detection technology of cancers.

The emergence of liquid biopsy technology has solved the above problems and shortened the time to cancer diagnosis. Liquid biopsy is not only a technique, but also a clinical solution. The liquid biopsy has the advantages of reducing the harm of tissue biopsy through non-invasive sampling, effectively prolonging the survival period of patients, and being cost-effective. For the liquid biopsy, tissues are relatively easy to obtain, and this is non-invasive to patients. However, the amount of free DNA in plasma is small and free DNA is prone to degradation. Therefore, it is relatively difficult to detect the methylation of genes in plasma. Not only the pretreatment process of the sample is extremely important, including the collection of plasma and the recovery rate and integrity of bis-DNA, but also a high sensitivity of the subsequent PCR amplification detection system is required. Therefore, there are two requirements for the development of such detection kits: the stability of sample during pretreatment and the accuracy of a PCR amplification detection system. Current detection products cannot meet these requirements.

SUMMARY OF THE INVENTION

The purpose of the present invention is to address the above-mentioned shortcomings in the prior art and to provide a combination of DNA methylation markers and the use thereof, primers and a kit for early detection of ovarian cancer. The primers and kit have the characteristics of high detection accuracy, and can provide a reliable reference for the clinical diagnosis of ovarian cancer. The detection primers and kit can use plasma as the detection sample, and do not cause damage to patients and is more easily accepted by patients.

The technical scheme of the present invention is described in detail as follows:

In a first aspect, the present invention provides a combination of DNA methylation markers, comprising at least one methylated fragment of each of the following four genes, including PCDHB18P, CDO1, HOXA9 and LYPD5:
PCDHB18P gene:
chr5:141235136-141235232: SEQ ID NO: 1,
chr5:141235796-141235918: SEQ ID NO: 2,
chr5:141235982-141236064: SEQ ID NO: 3;
CDO1 gene:
Chr5:115816656-115816755: SEQ ID NO: 4,
Chr5:115816502-115816579: SEQ ID NO: 5,
Chr5:115816382-115816460: SEQ ID NO: 6;
HOXA9 gene:
chr7:27166431-27166523: SEQ ID NO: 7,
chr7:27166020-27166126: SEQ ID NO: 8,
chr7:27165835-27165919: SEQ ID NO: 9;
and LYPD5 gene:
chr19:43820817-43820923: SEQ ID NO: 10,
chr19:43820625-43820694: SEQ ID NO: 11,
chr19:43820271-43820377: SEQ ID NO: 12.

Through combined screening for the types of ovarian cancer-related genes and the methylated region of each gene, the above four target genes (or referred to as targeted genes, marker genes) and their corresponding functional optimal methylated regions are finally screened out. The interpretation threshold can be determined by the complementarity of the methylation results for the methylated region of each target gene. When the results for each methylated region are combined with each other to be used as markers for early detection of ovarian cancer, the detection result has a high positive predictive value and high accuracy, and can provide clinicians with auxiliary diagnostic reference.

Optionally or preferably, the above combination of markers consists of the following methylated fragments:
PCDHB18P gene: chr5:141235796-141235918: SEQ ID NO: 2;
CDO1 gene: Chr5:115816656-115816755: SEQ ID NO: 4;
HOXA9 gene: chr7:27165835-27165919: SEQ ID NO: 9;
and LYPD5 gene: chr19:43820625-43820694: SEQ ID NO: 11.

In a second aspect, the present invention provides the use of the combination of markers in the preparation of a reagent for early screening and diagnosis of ovarian cancer.

In a third aspect, the present invention provides a detection primer set for early screening and diagnosis of ovarian cancer, comprising target gene detection primers for correspondingly detecting the methylated statuses of the methylated fragments in the above combination of markers, wherein each of the target gene detection primers has a nucleotide sequence with the 5' terminus having a sequence with a length of 5-10 bp which is complementary to and paired with the 3' terminus but is not paired with CG bases at the end of the 3' terminus; and the nucleotide sequence of each of the target gene detection primers has a Tm value which is 2-4° C. higher than the annealing temperature of a PCR reaction system.

The nucleotide sequence of the target gene detection primer has a clasp design structure. First, because the Tm value of the hairpin structure is higher than the annealing temperature, the target gene detection primer preferentially maintains itself to form a clasp structure rather than forming double-strands with other primers during the annealing process, and then a primer dimer does not form, which ensures that the amplification between different target gene detection primers will not cause interference, and there is an obvious advantage for the amplification of multiple primers. Second, the clasp structure has a high specificity. Because the binding free energy ΔG of the detection primer to the nucleotide sequence of the methylated region of the target gene is greater than the free energy of the hairpin formed by the primer itself by ΔG 5-10 kcal mol$^{-1}$, and then when the 3' terminus of the detection primer has mismatched bases, the detection primer having the clasp structure is almost difficult to bind to an unmethylated sequence, keeping the primer amplification with a better specificity.

Optionally or preferably, in the above detection primer set, the nucleotide sequence of the target gene detection primer has a locked nucleic acid modified base.

The locked nucleic acid modification method is beneficial to increase the binding free energy of the detection primer to the target gene sequence template by 10-20 ΔGkcal mol$^{-1}$, improves the capture efficiency of the primer and the target gene template, and increases the detection sensitivity, so that a plasma sample can be used. The free DNA in plasma is fragmented (about 150 bp), and the content thereof is lower than 10 ng, which can still be detected.

Optionally or preferably, in the above detection primer set, the nucleotide sequences of the target gene detection primers are shown below:

for PCDHB18P target gene:
the nucleotide sequences of detection primers for chr5: 141235136-141235232: SEQ ID NOs: 13-14,
the nucleotide sequences of detection primers for chr5: 141235796-141235918: SEQ ID NOs: 16-17,
the nucleotide sequences of detection primers for chr5: 141235982-141236064: SEQ ID NOs: 19-20;
for CDO1 target gene:
the nucleotide sequences of detection primers for Chr5: 115816656-115816755: SEQ ID NOs: 22-23,
the nucleotide sequences of detection primers for Chr5: 115816502-115816579: SEQ ID NOs: 25-26,
the nucleotide sequences of detection primers for Chr5: 115816382-115816460: SEQ ID NOs: 28-29;
for HOXA9 target gene:
the nucleotide sequences of detection primers for chr7: 27166431-27166523: SEQ ID NOs: 31-32,
the nucleotide sequences of detection primers for chr7: 27166020-27166126: SEQ ID NOs: 34-35,
the nucleotide sequences of detection primers for chr7: 27165835-27165919: SEQ ID NOs: 37-3 8;
and for LYPD5 target gene:
the nucleotide sequences of detection primers for chr19: 43820817-43820923: SEQ ID NOs: 40-41,
the nucleotide sequences of detection primers for chr19: 43820625-43820694: SEQ ID NOs: 43-44,
the nucleotide sequences of detection primers for chr19: 43820271-43820377: SEQ ID NOs: 46-47.

In a fourth aspect, the present invention provides a detection kit for early screening and diagnosis of ovarian cancer, comprising any one of the detection primer sets described above.

Optionally or preferably, the above kit further comprises target gene detection probes for correspondingly detecting the methylated statuses of the methylated fragments in the above combination of markers, wherein the nucleotide sequences of the target gene detection probes are shown below:

for PCDHB18P gene: the nucleotide sequence of a detection probe for chr5:141235136-141235232: SEQ ID NO: 15,
the nucleotide sequence of a detection probe for chr5: 141235796-141235918: SEQ ID NO: 18,
the nucleotide sequence of a detection probe for chr5: 141235982-141236064: SEQ ID NO: 21;
for CDO1 gene:
the nucleotide sequence of a detection probe for Chr5: 115816656-115816755: SEQ ID NO: 24,
the nucleotide sequence of a detection probe for Chr5: 115816502-115816579: SEQ ID NO: 27,
the nucleotide sequence of a detection probe for Chr5: 115816382-115816460: SEQ ID NO: 30;
for HOXA9 gene:
the nucleotide sequence of a detection probe for chr7: 27166431-27166523: SEQ ID NO: 33,
the nucleotide sequence of a detection probe for chr7: 27166020-27166126: SEQ ID NO: 36,
the nucleotide sequence of a detection probe for chr7: 27165835-27165919: SEQ ID NO: 39; and for LYPD5 gene:
the nucleotide sequence of a detection probe for chr19: 43820817-43820923: SEQ ID NO: 42,
the nucleotide sequence of a detection probe for chr19: 43820625-43820694: SEQ ID NO: 45,
the nucleotide sequence of a detection probe for chr19: 43820271-43820377: SEQ ID NO: 48.

The target gene detection probe also has a clasp structure, and the difference over the target gene detection primer is that a sequence with a length of 5-10 bp which is complementary to and paired with bases at the end near the 3' terminus is added at the 5' terminus of the nucleotide sequence. The Tm value of the hairpin structure should be higher than the annealing temperature in the PCR reaction system by 5-6° C., and meanwhile, the locked nucleic acid modified form is added. The objective is to increase the binding free energy of the primer to the sequence template by ΔG 15-25 kcal mol$^{-1}$, and improve the probe to capture low-copy target-methylated regions in the plasma free DNA. Moreover, the target gene detection probe having the clasp structure has another advantage, that is, after labeling with the fluorophore and the quenching group, the fluorophore and the quenching group of the sequence are closer, the mutual absorption effect of fluorescence is better, and no additional background fluorescence is generated. Therefore, the low fluorescence background also does not lead to a primer dimer. The target gene detection probe having the clasp structure has a third advantage, that is, it has very high specificity. Because the probe has a clasp design structure, the sequence itself is difficult to bind to unmethylated sequences, which ensures that the probe sequence would only bind to matched methylated sequences. The target gene detection probe having the clasp structure has a fourth advantage, that is, it is suitable for multiple amplification reactions. The probe sequences are labeled with different fluorophores, so that they can be applied to the combined synchronous detection of multiple genes. Meanwhile, each gene can be independently interpreted to show the methylation status of each gene in different samples, and finally a functional complementary combination detection can be performed.

Optionally or preferably, the above kit further comprises internal reference gene detection primers and an internal reference gene detection probe for an internal reference gene GAPDH, wherein the internal reference gene detection primers have nucleotide sequences as shown in SEQ ID NOs: 49-50, and the internal reference gene detection probe has a nucleotide sequence as shown in SEQ ID NO: 51.

Optionally or preferably, in the above kit, the nucleotide sequences of the target gene detection probe and the internal reference gene detection probe are labeled with fluorophores at the 5' terminus and are labeled with quenching groups at the 3' terminus, wherein the labeled fluorophores are different between the target gene detection probes and between the internal reference gene detection probes in the same detection system.

The fluorophores include, but are not limited to, FAM, ROX, CY5 and HEX, and the quenching groups include but are not limited to BHQ1 and BHQ2.

The target gene detection probes labeled with the different fluorescence channels can be put in one tube for reaction to ensure the best amplification efficiency of different target genes in the sample. The fluorescence curve is a standard S-shaped amplification curve, and the fluorescence curve keeps the same trend with the single amplification curve of each gene.

Optionally or preferably, the above kit further comprises a PCR reaction solution, wherein each one-person-portion of the PCR reaction solution is composed of 1-1.5 µL of Taq DNA polymerase with methylation characteristics at a concentration of 1 U/µL, 5-8 µL of dNTPs at a concentration of 10 mM, 3-6 µL of $Mg^{2+}$ at a concentration of 2-5 mM, 5 µL of 10×DNA polymerase buffer and purified water made up to 25 µL.

Compared with the prior art, the present invention has the following beneficial effects:

1. In the present invention, four ovarian cancer-related molecular marker genes, including PCDHB18P, CDO1, HOXA9 and LYPD5 are screened out, and the optimal methylation region in each gene which can be complementary to each other after combination for early detection of ovarian cancer is screened out and determined. The screened regions include not only the promoter region of the gene, but also the coding region of the gene. Due to the diversity and heterogeneity of ovarian cancer, the detection process is carried out by the sample pretreatment technology and the functional complementary multi-gene methylation combined detection technology. This detection process significantly improves the sensitivity of ovarian cancer detection, and meanwhile maintains a high specificity for normal ovarian cells and benign ovarian tumors. The detection composition detects patients with possible gynecological malignant tumors early through molecular epigenetic methods using methylation detection technology, and the result is very accurate, and can provide clinicians with auxiliary diagnostic reference for early prophylactic treatment.

2. For the methylated regions of the four combined target genes, specific primers and probes are designed, all of which have a clasp design structure and a locked nucleic acid modification form, and can double-recognize the methylated templates (the primers and probes capture the methylated region templates simultaneously), thereby enhancing the sensitivity and specificity of the PCR amplification system and reducing the detection error. Especially in the case where plasma is used as the sample, the amount of DNA is small, and the amount of DNA methylation is smaller, it is crucial to improve the sensitivity. The present invention uses a special design form of primers and probes, and the objective is to increase the capture efficiency of the template in the plasma free DNA, and to obtain accurate detection results with a small amount of samples, thereby the present invention is more suitable for clinical application.

All detection systems composed of the primers and probes can also use multi-gene multi-channel fluorescence detection methods, use five fluorescent probe labels and accurately recognize methylated sequences through specific primers and probes, and use the optimal PCR reaction solution, to accurately detect methylated sites in PCDHB18P, CDO1, HOXA9 and LYPD5 genes and complete detection of methylated sites in multiple genes in batches. The detection method is simple to operate and intuitive to interpret, and results can be obtained within 8 hours. Universal fluorescence quantitative PCR instruments can meet the detection requirements. It is achieved that the experimental process uses a one-stop fully enclosed form, which is easier to operate and avoids the possibility of cross-contamination.

3. The detection primers and probes and kits can use plasma as a sample, which provides another approach for early detection of ovarian cancer based on plasma free DNA analysis, overcoming the problem of intratumor heterogeneity. In the design of target gene detection primers and probes, the clasp structure is used, which increases the sensitivity and specificity of amplification. In the kit, the PCR reaction solution is expanded to 25 µL, and the total reaction system reaches 50 µL, which enhances the amplification ability of the PCR reaction system and capture efficiency of low-copy methylated templates.

4. The kit combines specific primers and probes, sample pretreatment reagents, Taq polymerase in the PCR reaction solution, etc., to ensure that the kit maintains a high sensitivity for low-concentration templates and has very high sensitivity for the detection of early ovarian cancer when used. The high detection sensitivity of this kit is suitable for early detection of ovarian cancer.

DETAILED DESCRIPTION OF EMBODIMENTS

The technical solutions of the present invention will be explained and described in detail below in conjunction with the accompanying drawings and the preferred specific examples, so that those skilled in the art can better understand and implement the present invention.

EXAMPLE 1

The Illumina Infinium MethylationEPIC BeadChip (containing 853,307 CpG sites) was used to screen the methylated genes of ovarian cancer by selecting 20 paraffin-embedded ovarian cancer tissue samples and 20 paraffin-embedded ovarian benign tissue samples.

Using commercial nucleic acid extraction or purification reagents and methylation detection sample pretreatment kits, the above 40 tissue samples were subjected to the extraction of genomic DNA and the process of DNA bisulfite conversion to obtain qualified, converted bis-DNA for the subsequent methylation chip screening and detection. Through the significant methylation difference locus algorithm, the results of ovarian cancer samples and ovarian benign samples were compared and analyzed, and the first four genes in deltaBeta (the methylation level of ovarian cancer tissue samples the methylation level of ovarian benign control samples; PCDHB18P=0.895, CDO1=0.818, HOXA9=0.812, and LYPD5=0.807) were screened out. Due to the large regional distribution of CpG in each gene, it is required to perform RT-PCR for verification and analysis of the particular methylation position of each gene. Finally, in each gene, three methylated regional fragments were determined, as shown in SEQ ID NOs: 1-2.

EXAMPLE 2

For the methylation regions of four target genes screened in Example 1, primers were designed and screened according to the specific sequences of the methylation regions to obtain the specific nucleotide sequences of the methylation region detection primers and probes, as shown in Table 1.

TABLE 1

Sequences of detection primers and probes corresponding to different methylated regions of target genes

| | | |
|---|---|---|
| PCDHB18P-F1 | atccaaaATTGGATTAATTTTT+G+GATCG | SEQ ID NO: 13 |
| PCDHB18P-R1 | tttaggttCAATATAATC+C+CAAACCTAAACG | SEQ ID NO: 14 |
| PCDHB18P-FP1 | FAM-ccgccaTAAC+GTTA+ATA+GTCGT+GGATGGCGG-BHQ1 | SEQ ID NO: 15 |
| PCDHB18P-F2 | ataataataaAAAT+G+A+A+T+AT+AAT+ATT+ATTA+TTATCG | SEQ ID NO: 16 |
| PCDHB18P-R2 | tttttattttAAA+ATTT+AA+AT+AA+AA+ATAA+A+A+ACG | SEQ ID NO: 17 |
| PCDHB18P-FP2 | FAM-ttaacgAATC+GTGTTG+GTTTTC+GAC+GTTAA-BHQ1 | SEQ ID NO: 18 |
| PCDHB18P-F3 | ttaataccAGAT+AG+AG+ATTT+AGGT+ATT+AACG | SEQ ID NO: 19 |
| PCDHB18P-R3 | tatttgttCCA+A+A+AA+A+ATA+A+A+A+ACAAATACG | SEQ ID NO: 20 |
| PCDHB18P-FP3 | FAM-taaaacgTTAT+TCGT+TGT+TGTCGT+TTTA-BHQ1 | SEQ ID NO: 21 |
| CDO1-F1 | aaaaaccTTT+TGGG+TGGT+TTTTCG | SEQ ID NO: 22 |
| CDO1-R1 | ggaggatgCT+ATAA+A+ATTCATCC+TCCCG | SEQ ID NO: 23 |
| CDO1-FP1 | ROX-aacgaccTCGT+TT+TTT+TT+TCGAGGGTCGTT-BHQ2 | SEQ ID NO: 24 |
| CDO1-F2 | caaaaacGT+TTT+TTGTTGT+TTT+TGCG | SEQ ID NO: 25 |
| CDO1-R2 | tgtgtgtGCT+AA+ACAA+ACAC+ACACG | SEQ ID NO: 26 |
| CDO1-FP2 | ROX-aaaatacTTT+TTACGT+TTCGGTAT+TTT-BHQ2 | SEQ ID NO: 27 |
| CDO1-F3 | ataaaaaGTTCGT+TTAGTT+TTTT+TATCG | SEQ ID NO: 28 |
| CDO1-R3 | agatggaCTTCG+ATCTAT+TCCATCTCG | SEQ ID NO: 29 |
| CDO1-FP3 | ROX-taactacgTGAG+ACGCG+CGCGTAGTTA-BHQ2 | SEQ ID NO: 30 |
| HOXA9-F1 | cctttctcG+TTAGT+TGA+TGAGA+AAGGCG | SEQ ID NO: 31 |
| HOXA9-R1 | tataattaT+T+TT+AA+A+AACCTAA+TT+AA+TTATACG | SEQ ID NO: 32 |
| HOXA9-FP1 | CY5-ccacgcaTG+GGCGCG+CGTGTGCGTGG-BHQ2 | SEQ ID NO: 33 |
| HOXA9-F2 | aaaacttaTAGT+TT+AATT+TTT+TTAAGTTT+TCG | SEQ ID NO: 34 |
| HOXA9-R2 | ttagtttgCA+AAA+ACC+ACACA+AA+CTAACG | SEQ ID NO: 35 |
| HOXA9-FP2 | CY5-attcgtttaTTA+CGGCG+AGGTA+A+ACGAAT-BHQ2 | SEQ ID NO: 36 |
| HOXA9-F3 | aaacccctcTTTA+TGTG+AGGGG+TT+TCG | SEQ ID NO: 37 |
| HOXA9-R3 | tgattaattAACTA+TT+TTATA+TCACAAT+TAA+TCACG | SEQ ID NO: 38 |
| HOXA9-FP3 | CY5-aacgcgaatTCGTAT+TCGT+ACGCGGG+AT+TCGCGTT-BHQ2 | SEQ ID NO: 39 |
| LYPD5-F1 | ttttcaatTG+AAA+TTTGA+TAAT+TGA+AAACG | SEQ ID NO: 40 |
| LYPD5-R1 | ttttttgAA+ATCCCT+T+TA+ACAA+A+AA+ACG | SEQ ID NO: 41 |
| LYPD5-FP1 | HEX-attaaaaaGTTT+TTATT+TTCGT+ACGTATT+TT+TTAAT-BHQ1 | SEQ ID NO: 42 |
| LYPD5-F2 | acccaatTT+T+T+TA+TAGGT+TA+TTGGGTCG | SEQ ID NO: 43 |
| LYPD5-R2 | tattttagCCCA+AA+AA+TCACT+A+AA+ATACG | SEQ ID NO: 44 |
| LYPD5-FP2 | HEX-aacgaatAGCG+TGCG+TT+TT+TG+ATTCGTT-BHQ1 | SEQ ID NO: 45 |
| LYPD5-F3 | cacataatGGTG+TG+TGTAATATTATGTGCG | SEQ ID NO: 46 |
| LYPD5-R3 | gttgggaCAAA+ACA+TCCC+AACCG | SEQ ID NO: 47 |
| LYPD5-FP3 | HEX-acgcaacgTCGTGCG+AAT+GGTG+ACGT+TGCGT-BHQ1 | SEQ ID NO: 48 |
| GAPDH-F | AGGTTAAATATAGTTGTTGA | SEQ ID NO: 49 |

TABLE 1-continued

Sequences of detection primers and probes
corresponding to different methylated regions of target genes

| GAPDH-R | CAACCCAAACCCCCAAC | SEQ ID NO: 50 |
| --- | --- | --- |
| GAPDH-FP | Joe-TAGTTGGGGGTTTGGGTT-BHQ1 | SEQ ID NO: 51 |

Notes: F stands for a forward detection primer, R stands for a reverse detection primer, and FP stands for a detection probe. In this table, the probe sequences as shown have been labeled with fluorophores and quenching groups.

Using the primers and probes listed in the above Table 1, a detection kit (PCR amplification system kit) was prepared, the detection kit comprising a PCR reaction solution, a mixture solution of primers and probes, a positive quality control product and a negative quality control product, and the components are listed in Table 2 below:

TABLE 2

Composition of PCR amplification system kits

| Components | Main ingredients |
| --- | --- |
| PCR reaction solution | 1-1.5 µL of Taq DNA polymerase with methylation characteristics at a concentration of 1 U/µL, 5-8 µL of dNTPs at a concentration of 10 mM; $Mg^{2+}$ 3-6 µL at a concentration of 2-5 mM; 5 µL of 10× DNA polymerase buffer; Purified water making up to 25 µL. |
| Mixed solution of primers and probes | Forward and reverse primers and probes for the methylated region of PCDHB18P gene, Forward and reverse primers and probes for the methylated region of CDO1 gene, Forward and reverse primers and probes for the methylated region of HOXA9 gene, Forward and reverse primers and probes for the methylated region of LYPD5 gene, Primers and probes for GAPDH gene. |
| Positive quality control | Genomic DNA fragments of different malignant tumor cell lines |
| Negative quality control | Purified water |

128 ovarian cancer samples with known and clear pathological information were selected: 62 samples identified as high-grade serous ovarian cancer, 28 samples identified as low-grade serous ovarian cancer, 13 samples identified as mucinous ovarian cancer, 13 samples identified as ovarian endometrioid carcinoma, and 12 samples identified as ovarian clear cell carcinoma; and 110 ovarian benign samples were selected.

The above samples were obtained from reserved plasma samples.

I. Methylation Pretreatment for Samples

Fragments of free DNA in plasma are mostly around 150 bp, and the content thereof is very low (lower than 10 ng). Therefore, sample pretreatment reagents and subsequent PCR reaction solutions are important to determine whether changes in gene methylation in plasma free DNA can be detected.

The methylation pretreatment reagent for a sample includes a cell genomic DNA extraction reagent and a DNA bisulfite conversion reagent. When using the sample methylation pretreatment reagent, two processes are included, one is the extraction process of plasma free DNA, and the other is the conversion process of bisulfite, and quality control should be well done in each step.

1. A nucleic acid extraction or purification reagent in a plasma free DNA extraction kit was used as a plasma free DNA extraction reagent. Free DNA was extracted from the above 238 plasma samples, and meanwhile DNA quality was monitored. DNA with a concentration of above 0.3 ng/ul and a total amount of 6 ng-10 ng were extracted from 2 mL of plasma, and ensure that the quality of the extracted free DNA meets the requirements.

2. Using a bisulfite conversion kit (methylation detection sample pretreatment kit) as the DNA bisulfite conversion reagent, bisulfite conversion was performed on the extracted DNA, wherein unmethylated cytosine (C) in DNA was converted to uracil (U), and methylated cytosine (C) remained unchanged, and then the converted bis-DNA was obtained.

Several important quality control indicators in the conversion process: one is to monitor the amount and integrity of free DNA in the sample, the second is to monitor the recovery rate of the converted bis-DNA, and the third is to monitor the integrity of the converted bis-DNA. So that high-quality bis-DNA were provided for subsequent PCR amplification reactions.

I. Fluorescence Quantitative PCR Amplification of bis-DNA

1. Formulation of PCR reaction solution and mixed solution of primers and probes

TABLE 3

PCR reaction solution (25 µL/person)

| Components | Adding amount/person (µL) |
| --- | --- |
| DNA polymerase with methylation characteristics (1 U/µL) | 1.5 |
| dNTPs (10 mM) | 7 |
| $Mg^{2+}$ (2-5 mM) | 5 |
| 10× DNA polymerase buffer | 5 |
| Purified water | making up to 25 µL |

In the above PCR reaction system, the important component is the methylation-specific Taq polymerase, which has the following advantages: the template sequence after the bisulfite conversion is amplified, the sequence after the conversion can be specifically recognized, and the amplification efficiency of the primers on the sequence after the conversion is improved. Less Taq enzyme reduces the amplification efficiency, and too much Taq enzyme can easily cause non-specific amplification. Therefore, the selection of the amount of Taq enzyme directly affects the results of PCR amplification. In addition, the proportion of dNTPs, $Mg^{2+}$, and 10×DNA polymerase buffer in the system also directly affects the amplification efficiency of the primer-probe combination.

The PCR reaction system can specifically amplify bis-DNA after the bisulfite conversion, and is used for multiplex primer amplification. Therefore, the amplification ability of the PCR reaction solution is particularly important, and it needs to ensure that the amplification efficiency of the primers and probe of each gene in the PCR reaction system is consistent with that of its corresponding single amplification. Therefore, it is necessary to screen, test and verify methylation-specific Taq polymerases modified by different antibodies and the proportion to dNTPs, $Mg^{2+}$, and 10×DNA polymerase buffer components, in order to determine the composition of the final PCR reaction solution and that the amplification efficiency of the PCR reaction system is optimal.

TABLE 4

Mixed solution of primers and probes (5 μL/person)

| Components | Adding amount/ person (μL) |
|---|---|
| CDO1/CELF1/HAND2/HS3ST2-F (100 μM) | 0.2-0.4 |
| CDO1/CELF1/HAND2/HS3ST2-R (100 μM) | 0.1-0.3 |
| CDO1/CELF1/HAND2/HS3ST2-FP (100 μM) | 0.15-0.25 |
| GAPDH gene-F (100 μM) | 0.05 |
| GAPDH gene-R (100 μM) | 0.05 |
| GAPDH gene-FP (100 μM) | 0.05 |
| Purified water | making up to 5 μL |

1. Addition of Samples

Since the sample used is plasma free DNA and the content thereof is extremely low, the PCR reaction solution in Table 3 was expanded to 25 μL, and the PCR amplification reaction system was expanded to 50 μL. The template for amplifying bis-DNA needs to be expanded to 20 μL to further improve the detection rate of the methylated target gene in plasma free DNA.

20 μL of negative quality control, positive quality control and the converted Bis-DNA clinical samples were respectively added to the above formulated system. PCR reaction was carried out and the conditions are: pre-denaturation at 96° C. for 5 min; denaturation at 94° C. for 15 s, annealing and extension at 60° C. for 35 s, 45 cycles; keeping at 25° C. for 10 min.

1. The Amplification Procedure is as Follows

Step 1: pre-denaturation at 96° C. for 5 min;
Step 2: denaturation at 94° C. for 15 s, annealing and extension at 60° C. for 35 s, 45 cycles;
Step 3: 25° C., 10 min;
Signal collection, FAM, HEX, ROX, Joe and CY5 signals were collected at 60° C.

Figure 1:
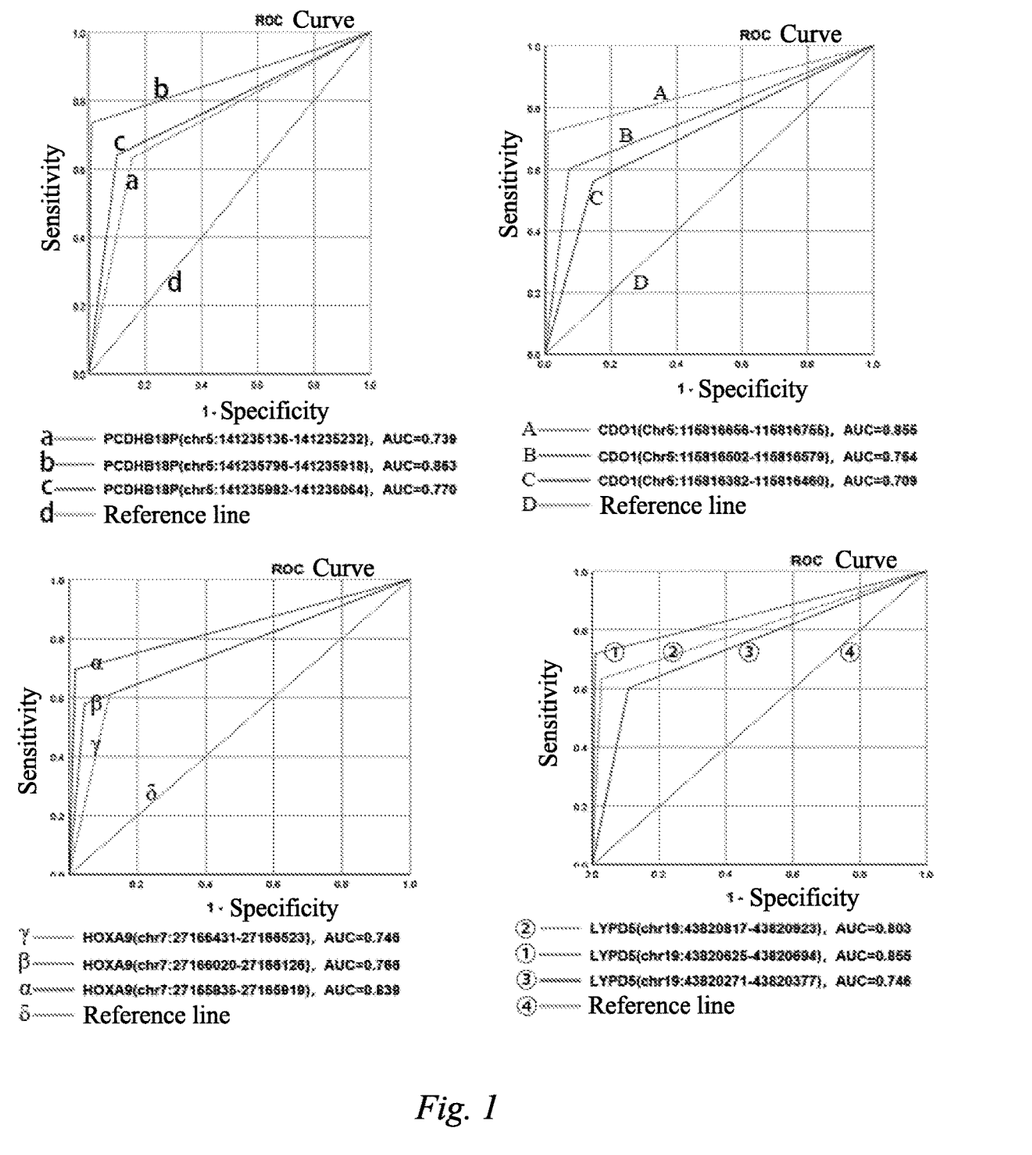
FIG. 1 shows the ROC curves of the screening of methylated regions of each of the target genes, including PCDHB18P, CDO1, HOXA9 and LYPD5.

1. Interpretation of Results (1) interpretation is performed according to the inflection point of the internal standard curve, and when the internal standard channel has an S-shaped amplification curve and the Ct value≤35.4, the result is valid;
(2) interpretation is performed according to the inflection point of the internal standard curve, and the amplification Ct values of PCDHB18P, CDO1, HOXA9 and LYPD5 are read successively; and
(3) the thresholds and performance (including specificity, sensitivity, negative predictive value, and positive predictive value) of multiple methylated regions in the target genes are determined by integrating the Ct values of the above 4 genes and according to the ROC curve, to determine the optimal methylated region and the interpretation way for the 4 target genes.

1. Analysis of Detection Results

A total of 238 samples were detected using the above kit reaction system, including 128 samples of ovarian cancer and 110 samples of benign ovary.

Comparing the clinicopathological results, in 238 plasma samples, the positive rate of PCDHB18P (chr5:141235136-141235232) in ovarian cancer was 63.3% (81/128), the specificity thereof in benign samples was 84.5% (93/110), and the ROC area thereof was 0.739;

the positive rate of PCDHB18P (chr5:141235796-141235918) in ovarian cancer was 73.4% (94/128), the specificity thereof in benign samples was 99.1% (109/110), and the ROC area thereof was 0.863;

the positive rate of PCDHB18P (chr5:141235982-141236064) in ovarian cancer was 64.1% (82/128), the specificity thereof in benign samples was 90% (99/110), and the ROC area thereof was 0.770;

the positive rate of CDO1 (Chr5:115816656-115816755) in ovarian cancer was 71.9% (92/128), the specificity thereof in benign samples was 99.1% (109/110), and the ROC area thereof was 0.855;

the positive rate of CDO1 (Chr5:115816502-115816579) in ovarian cancer was 60.2% (77/128), the specificity thereof in benign samples was 92.7% (102/110), and the ROC area thereof was 0.764;

the positive rate of CDO1 (Chr5:115816382-115816460) in ovarian cancer was 56.3% (72/128), the specificity thereof in benign samples was 85.5% (94/110), and the ROC area thereof was 0.709;

the positive rate of HOXA9 (chr7:27166431-27166523) in ovarian cancer was 60.9% (78/128), the specificity thereof in benign samples was 88.2% (97/110), and the ROC area thereof was 0.746;

the positive rate of HOXA9 (chr7:27166020-27166126) in ovarian cancer was 57.8% (74/128), the specificity thereof in benign samples was 95.5% (105/110), and the ROC area thereof was 0.766;

the positive rate of HOXA9 (chr7:27165835-27165919) in ovarian cancer was 69.5% (89/128), the specificity thereof in benign samples was 98.2% (108/110), and the ROC area thereof was 0.839;

the positive rate of LYPD5 (chr19:43820817-43820923) in ovarian cancer was 63.3% (81/128), the specificity thereof in benign samples was 97.3% (107/110), and the ROC area thereof was 0.803;

the positive rate of LYPD5 (chr19:43820625-43820694) in ovarian cancer was 71.9% (92/128), the specificity thereof in benign samples was 99.1% (109/110), and the ROC area thereof was 0.855;

and the positive rate of LYPD5 (chr19:43820271-43820377) in ovarian cancer was 60.2% (77/128), the specificity thereof in benign samples was 89.1% (98/110), and the ROC area thereof was 0.746.

After comparative analysis of the multiple methylated regions of PCDHB18P, CDO1, HOXA9 and LYPD5, the optimal methylated region selected from PCDHB18P gene was chr5:141235796-141235918, the optimal methylated region selected from CDO1 gene was Chr5:115816656-115816755, the optimal methylation region selected from HOXA9 gene was chr7:27165835-27165919, and the optimal methylation region selected from LYPD5 was chr19: 43820625-43820694.

Combined detection of the optimal methylated regions of PCDHB18P, CDO1, HOXA9 and LYPD5 was carried out, and different gene combinations were compared and interpreted, and finally the optimal interpretation way was obtained. The following results as shown in Table 5 can be obtained:

TABLE 5

Combined detected performance of optimal methylated regions of two target genes

| | PCDHB18P/ CDO1 | PCDHB18P/ HOXA9 | PCDHB18P/ LYPD5 | CDO1/ HOXA9 | CDO1/ LYPD5 | HOXA9/ LYPD5 |
|---|---|---|---|---|---|---|
| Sensitivity (any one of genes is positive) | 82.8% (106/128) | 84.4% (108/128) | 84.4% (108/128) | 85.9% (110/128) | 85.9% (110/128) | 85.2% (109/128) |
| Specificity (any one of genes is positive) | 98.2% (108/110) | 98.2% (108/110) | 98.2% (108/110) | 98.2% (108/110) | 99.1% (109/110) | 98.2% (108/110) |
| Sensitivity (both genes are positive) | 62.5% (80/128) | 58.6% (75/128) | 60.9% (78/128) | 55.5% (71/128) | 60.9% (78/128) | 56.3% (72/128) |
| Specificity (both genes are positive) | 100% (110/110) | 99.1% (109/110) | 100% (110/110) | 99.1% (109/110) | 99.1% (109/110) | 99.1% (109/110) |

TABLE 6

Combined detected performance of optimal methylated regions of three target genes

| | PCDHB18P/ CDO1/HOXA9 | PCDHB18P/ CDO1/LYPD5 | CDO1/HOXA9/ LYPD5 |
|---|---|---|---|
| Sensitivity (any one of genes is positive) | 89.8% (115/128) | 90.6% (116/128) | 93% (119/128) |
| Specificity (any one of genes is positive) | 98.2% (108/110) | 98.2% (108/110) | 98.2% (108/110) |
| Sensitivity (any two of genes are positive) | 70.3% (90/128) | 72.7% (93/128) | 68% (87/128) |
| Specificity (any two of genes are positive) | 98.2% (108/110) | 99.1% (109/110) | 99.1% (109/110) |
| Sensitivity (all three genes are positive) | 51.6% (66/128) | 57.8% (74/128) | 52.3% (67/128) |
| Specificity (all three genes are positive) | 100% (110/110) | 100% (110/110) | 99.1% (109/110) |

TABLE 7

Combined detected performance of optimal methylated regions of four target genes

| | PCDHB18P/CDO1/HOXA9/ LYPD5 |
|---|---|
| Sensitivity (any one of genes is positive) | 95.3% (122/128) |
| Specificity (any one of genes is positive) | 98.2% (108/110) |
| Sensitivity (any two of genes are positive) | 78.1% (100/128) |
| Specificity (any two of genes are positive) | 98.2% (108/110) |
| Sensitivity (any three of genes are positive) | 63.3% (81/128) |
| Specificity (any three of genes are positive) | 99.1% (109/110) |
| Sensitivity (all four genes are positive) | 50% (64/128) |
| Specificity (all four genes are positive) | 100% (110/110) |

Figure 2:
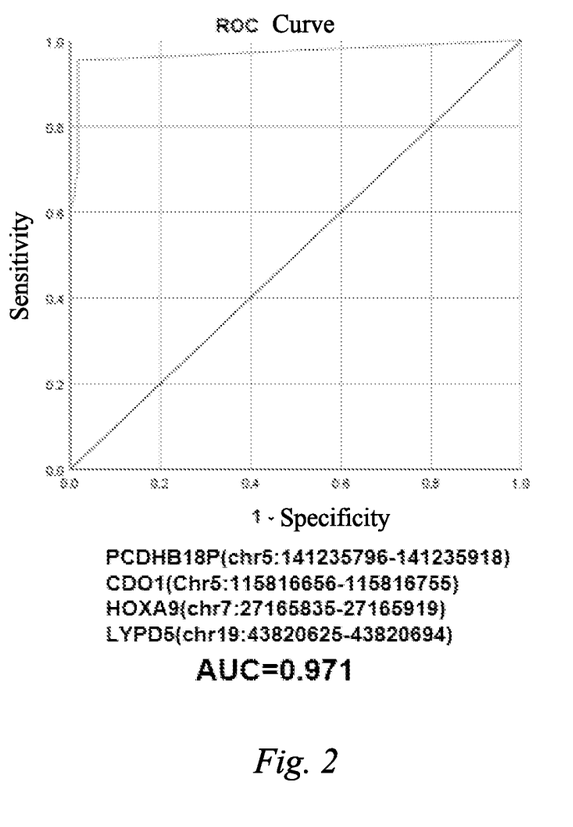
FIG. 2 shows the ROC curves of the combined detection of the optimal methylated regions of four target genes, including PCDHB18P, CDO1, HOXA9 and LYPD5.

In the data of the above three tables, when the optimal methylated regions of four target genes, including PCDHB18P, CDO1, HOXA9, and LYPD5, were combined detected, and if any one of genes was positive, the sample was interpreted as positive, the sensitivity and specificity in 283 plasma samples were overall optimal, wherein the sensitivity for ovarian cancer was 95.3% (122/128), the specificity for benign samples was 98.2% (108/110), and the detected ROC area was 0.971.

Meanwhile, the combined detection of the optimal methylated regions of four target genes, including PCDHB18P, CDO1, HOXA9 and LYPD5 (if any one of genes was positive, the methylation detection was interpreted as positive), was analyzed compared with a tumor molecular marker CA125 (a commonly used detection means in clinical practice) detection. The results of the comparative analysis are shown in Table 8. It can be seen from Table 8: the positive predictive value (0.984) from the combined detection of the methylation status of the optimal methylated regions of the four genes was significantly higher than that of the tumor molecular marker CA125 (0.736).

TABLE 8

Comparative analysis of combined detection of methylated regions and CA125 detection

| | PCDHB18P/CDO1/ HOXA9/LYPD5 Combined methylation detection | | Molecular markers for tumors CA125 detection | |
|---|---|---|---|---|
| | Negative | Positive | Negative | Positive |
| Benign ovary (n = 110) | 108 | 2 | 76 | 34 |
| High-grade serous ovarian cancer (n = 62) | 3 | 59 | 16 | 46 |
| Low-grade serous ovarian cancer (n = 28) | 2 | 26 | 8 | 20 |
| Mucinous ovarian cancer (n = 13) | 1 | 12 | 3 | 10 |
| Ovarian endometrioid carcinoma (n = 13) | 0 | 13 | 4 | 9 |
| Ovarian clear cell carcinoma (n = 12) | 0 | 12 | 2 | 10 |
| Sensitivity (ovarian cancer) | 95.3% | | 74.2% | |
| Specificity (benign ovary) | 98.2% | | 69.1% | |
| Positive predictive value | 0.984 | | 0.736 | |
| Negative predictive value | 0.947 | | 0.697 | |

Through sample research and test, it is proved that DNA methylation has a high positive predictive value for early detection of ovarian cancer, and the detection can be done with plasma samples. The present invention uses special primer and probe design skills (for specially capturing low-copy plasma free DNA fragments), and combined detection of multi-target gene methylation regions, which are functionally complementary, and significantly improve the detection of early ovarian cancer.

Herein, specific examples are used to describe the inventive concept in detail, and the description of the above examples is only used to help understand the core idea of the present invention. It should be pointed out that for those of ordinary skill in the art, any obvious modification, equivalent replacement or other improvement made should be included in the protection scope of the present invention without departing from the inventive concept.

What is claimed is:

1. A detection primer set for early screening and diagnosis of ovarian cancer, wherein the detection primer set comprises target gene detection primers for detecting the methylated statuses of a combination of methylated fragments,
wherein the combination of methylated fragments comprises at least one methylated fragment of each of the following four genes, including PCDHB18P, CDO1, HOXA9 and LYPD5:
wherein the methylated fragment for the PCDHB18P gene consists of the nucleotide sequence of:
SEQ ID NO: 1,
SEQ ID NO: 2, or
SEQ ID NO: 3;
wherein the methylated fragment for the CDO1 gene consists of the nucleotide sequence of:
SEQ ID NO: 4,
SEQ ID NO: 5, or
SEQ ID NO: 6;
wherein the methylated fragment for the HOXA9 gene consists of the nucleotide sequence of:
SEQ ID NO: 7,
SEQ ID NO: 8, or
SEQ ID NO: 9;
and wherein the methylated fragment for the LYPD5 gene consists of the nucleotide sequence of:
SEQ ID NO: 10,
SEQ ID NO: 11, or
SEQ ID NO: 12,
wherein each of the target gene detection primers has added at its 5' terminus a nucleotide sequence with a length of 5-10 bp which is complementary to and pairs with a nucleotide sequence at the 3' terminus of the same primer to form a hairpin structure, wherein the last two bases at the 3' terminus of each primer are a CG dinucleotide and the 5' terminal sequence does not pair with the CG bases at the end of the 3' terminus; and
wherein the nucleotide sequence of each of the target gene detection primers has a Tm value which is 2-4° C. higher than the annealing temperature at which the target gene detection primer anneals to the methylated fragment of the target gene in a PCR reaction system.

2. The detection primer set according to claim 1, wherein the combination of methylated fragments consists of:
(i) the methylated fragment in the PCDHB18P gene having the nucleotide sequence of: SEQ ID NO: 2;
(ii) the methylated fragment in the CDO1 gene having the nucleotide sequence of: SEQ ID NO: 4;
(iii) the methylated fragment in the HOXA9 gene having the nucleotide sequence of: SEQ ID NO: 9;
and (iv) the methylated fragment in the LYPD5 gene having the nucleotide sequence of: SEQ ID NO: 11.

3. The detection primer set according to claim 1, wherein the nucleotide sequence of each of the target gene detection primers has a locked nucleic acid modified base.

4. The detection primer set according to claim 1, wherein the nucleotide sequences of the target gene detection primers are shown below:
for PCDHB18P target gene:
the nucleotide sequences of detection primers for the methylated fragment of SEQ ID NO: 1 are SEQ ID NOs: 13-14,
the nucleotide sequences of detection primers for the methylated fragment of SEQ ID NO: 2 are SEQ ID NOs: 16-17,
the nucleotide sequences of detection primers for the methylated fragment of SEQ ID NO: 3 are SEQ ID NOs: 19-20;

for CDO1 target gene:
the nucleotide sequences of detection primers for the methylated fragment of SEQ ID NO: 4 are SEQ ID NOs: 22-23,
the nucleotide sequences of detection primers for the methylated fragment of SEQ ID NO: 5 are SEQ ID NOs: 25-26,
the nucleotide sequences of detection primers for the methylated fragment of SEQ ID NO: 6 are SEQ ID NOs: 28-29;

for HOXA9 target gene:
the nucleotide sequences of detection primers for the methylated fragment of SEQ ID NO: 7 are SEQ ID NOs: 31-32,
the nucleotide sequences of detection primers for the methylated fragment of SEQ ID NO: 8 are SEQ ID NOs: 34-35,
the nucleotide sequences of detection primers for the methylated fragment of SEQ ID NO: 9 are SEQ ID NOs: 37-38;

and for LYPD5 target gene:
the nucleotide sequences of detection primers for the methylated fragment of SEQ ID NO: 10 are SEQ ID NOs: 40-41,
the nucleotide sequences of detection primers for the methylated fragment of SEQ ID NO: 11 are SEQ ID NOs: 43-44,
the nucleotide sequences of detection primers for the methylated fragment of SEQ ID NO: 12 are SEQ ID NOs: 46-47.

5. A detection kit for early screening and diagnosis of ovarian cancer, wherein the detection kit comprises the detection primer set according to claim 1 and instructions for use thereof.

6. The detection kit according to claim 5, wherein the detection kit further comprises target gene detection probes for correspondingly detecting the methylated statuses of the methylated fragments, wherein the nucleotide sequence of the target gene detection probe is shown below:
for PCDHB18P gene:
the nucleotide sequence of a detection probe for the methylated fragment of SEQ ID NO: 1 is SEQ ID NO: 15,
the nucleotide sequence of a detection probe for the methylated fragment of SEQ ID NO: 2 is SEQ ID NO: 18,
the nucleotide sequence of a detection probe for the methylated fragment of SEQ ID NO: 3 is SEQ ID NO: 21;

for CDO1 gene:
the nucleotide sequence of a detection probe for the methylated fragment of SEQ ID NO: 4 is SEQ ID NO: 24,
the nucleotide sequence of a detection probe for the methylated fragment of SEQ ID NO: 5 is SEQ ID NO: 27,
the nucleotide sequence of a detection probe for the methylated fragment of SEQ ID NO: 6 is SEQ ID NO: 30;

for HOXA9 gene:
the nucleotide sequence of a detection probe for the methylated fragment of SEQ ID NO: 7 is SEQ ID NO: 33,
the nucleotide sequence of a detection probe for the methylated fragment of SEQ ID NO: 8 is SEQ ID NO: 36,
the nucleotide sequence of a detection probe for the methylated fragment of SEQ ID NO: 9 is SEQ ID NO: 39;

and for LYPD5 gene:
the nucleotide sequence of a detection probe for the methylated fragment of SEQ ID NO: 10 is SEQ ID NO: 42,
the nucleotide sequence of a detection probe for the methylated fragment of SEQ ID NO: 11 is SEQ ID NO: 45,
the nucleotide sequence of a detection probe for the methylated fragment of SEQ ID NO: 12 SEQ ID NO: 48.

7. The detection kit according to claim 6, wherein the detection kit further comprises internal reference gene detection primers and an internal reference gene detection probe for an internal reference gene GAPDH, wherein the nucleotide sequences of the internal reference gene detection primers are SEQ ID NOs: 49-50, and the nucleotide sequence of the internal reference gene detection probe is SEQ ID NO: 51.

8. The detection kit according to claim 7, wherein the nucleotide sequences of the target gene detection probe and the internal reference gene detection probe are labeled with fluorophores at the 5' terminus and are labeled with quenching groups at the 3' terminus, wherein the labeled fluorophores are different between the target gene detection probes and between the internal reference gene detection probes in the same detection system.

\* \* \* \* \*

UNITED STATES PATENT AND TRADEMARK OFFICE
CERTIFICATE OF CORRECTION

| | | |
|---|---|---|
| PATENT NO. | : 11,866,790 B2 | Page 1 of 1 |
| APPLICATION NO. | : 17/871119 | |
| DATED | : January 9, 2024 | |
| INVENTOR(S) | : Pei Liu and Linhai Wang | |

It is certified that error appears in the above-identified patent and that said Letters Patent is hereby corrected as shown below:

On the Title Page

(63) under Related U.S. Application Data, the text:
"Continuation of application No. PCT/CN2022/095437, filed on Jun. 9, 2022."
Should be replaced with:
--Continuation of application No. PCT/CN2022/095437, filed on May 27, 2022.--

In the Specification

In Column 1, Lines 9-14, under CROSS-REFERENCE TO RELATED APPLICATIONS, the text:
"This application claims benefit to International Patent Application No. PCT/CN2022/095437 filed on Jun. 9, 2022 which claims benefit under 35 U.S.C. § 119(b) of CN Application No. CN202210208334.2, filed on 3 Mar. 2022, the contents of each of which are incorporated herein by reference in their entireties."
Should be replaced with:
--This application claims benefit to International Patent Application No. PCT/CN2022/095437 filed on May 27, 2022, which claims benefit under 35 U.S.C. § 119(b) of CN Application No. CN202210208334.2, filed on 3 Mar. 2022, the contents of each of which are incorporated herein by reference in their entireties.--

Signed and Sealed this
Seventh Day of May, 2024

Katherine Kelly Vidal
*Director of the United States Patent and Trademark Office*